(12) United States Patent
Hsieh

(10) Patent No.: US 6,654,440 B1
(45) Date of Patent: Nov. 25, 2003

(54) METHODS AND APPARATUS FOR COMPUTED TOMOGRAPHY SCANNING USING A TWO-DIMENSIONAL RADIATION SOURCE

(75) Inventor: Jiang Hsieh, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/064,297

(22) Filed: Jun. 29, 2002

(51) Int. Cl.[7] .................................................. A61B 6/03
(52) U.S. Cl. ............................... 378/4; 378/19; 378/901
(58) Field of Search ............................. 378/4, 8, 15, 19, 378/901

(56) References Cited

U.S. PATENT DOCUMENTS

| 4,731,239 A | 3/1988 | Gordon |
|---|---|---|
| 5,762,608 A | 6/1998 | Warne et al. |
| 6,317,478 B1 | 11/2001 | Patch |
| 2002/0054659 A1 * | 5/2002 | Okumura et al. ............. 378/19 |

* cited by examiner

Primary Examiner—David V. Bruce
(74) Attorney, Agent, or Firm—Carl B. Horton, Esq.; Armstrong Teasdale LLP

(57) ABSTRACT

A method for collecting computed tomography (CT) scan data includes positioning a gantry at a first position, collecting a partial inverted-cone beam projection at a first detector cell at the first gantry position such that the first detector cell defines a focusing position in space, and collecting data from a second detector cell different from the first detector cell as the gantry rotates such that the focusing position remains substantially stationary in space.

69 Claims, 5 Drawing Sheets

METHODS AND APPARATUS FOR COMPUTED TOMOGRAPHY SCANNING USING A TWO-DIMENSIONAL RADIATION SOURCE

BACKGROUND OF INVENTION

This invention relates generally to computed tomography (CT) and, more particularly to methods and apparatus for collecting CT scan data.

In at least one known computed tomography (CT) imaging system configuration, an x-ray source projects a divergent, cone-shaped beam. After passing through the sample, the attenuated x-rays are then collected by an array of detectors which, due to the divergent nature of the beam, is much larger than the object being sampled. Such large detector arrays can be expensive. To lower the cost it is desirable to develop a CT scanner system capable of using a smaller detector array yet capable of scanning relatively large samples, such as a patient.

SUMMARY OF INVENTION

In one aspect, a method for collecting computed tomography (CT) scan data is provided. The method includes positioning a gantry at a first position, collecting a partial inverted-cone beam projection at a first detector cell at the first gantry position such that the first detector cell defines a focusing position in space, and collecting data from a second detector cell different from the first detector cell as the gantry rotates such that the focusing position remains substantially stationary in space.

In another aspect, a method for collecting CT scan data is provided. The method includes separating a sampling pattern into a plurality of simplified sampling geometries corresponding to inverted-cone beam trajectories of a plurality of individual detector elements, reconstructing an image volume for each inverted-cone beam trajectory, and combining the reconstructed image volumes into a final image based on a weighted summation of a plurality of the reconstructed image volumes.

In yet another aspect, a method for collecting CT scan data is provided. The method includes collecting x-ray projection samples that arise from x-rays that are perpendicular to the axis of rotation, collecting x-ray projection samples that arise from x-rays that are oblique to the axis of rotation, utilizing the projection samples arising from x-rays perpendicular to the axis of rotation to reconstruct an initial estimate of an object near the object's boundaries, synthesizing a plurality of oblique projections by forward-projection, and combining the synthesized oblique projection samples and the measured oblique projection samples with the initial estimate of the object to produce a complete cone beam reconstruction.

In still another aspect, a method for collecting CT scan data is provided. The method includes positioning a gantry at a first position, collecting a partial cone beam projection from a single source emitter at the first detector position such that the particular emitter defines a focal position in space, switching between a plurality of single source emitters as the gantry rotates so that the focal spot from which radiation emanates is substantially stationary in space, and collecting a partial cone beam from a second emitter at a second detector position.

In another aspect, a method for collecting CT scan data is provided. The method includes positioning a gantry at a first position, collecting an inverted-cone beam projection at a first detector cell at the first gantry position such that the first detector cell defines a focusing position in space, moving the gantry to a second position different from the first such that the source emitters are intermediate between the positions they occupied at the first gantry position, and collecting an inverted-cone beam projection at the second gantry position, at a detector cell that occupies substantially the same point in space defined by the first detector cell during the first data collection cycle.

In yet another aspect, a computer for collecting computed tomography (CT) scan data is provided. The computer is programmed to position a gantry at a first position, collect a partial inverted-cone beam projection at a first detector cell at the first gantry position such that the first detector cell defines a focusing position in space, and collect data from a second detector cell different from the first detector cell as the gantry rotates such that the focusing position remains substantially stationary in space.

In still another aspect, a computer for collecting CT scan data is provided. The computer is programmed to separate a sampling pattern into a plurality of simplified sampling geometries corresponding to inverted-cone beam trajectories of a plurality of individual detector elements, reconstruct an image volume for each inverted-cone beam trajectory, and combine the reconstructed image volumes into a final image based on a weighted summation of a plurality of the reconstructed image volumes.

In another aspect, a computer for collecting CT scan data is provided. The computer is programmed to collect x-ray projection samples that arise from x-rays that are perpendicular to the axis of rotation, collect x-ray projection samples that arise from x-rays that are oblique to the axis of rotation, utilize the projection samples arising from x-rays perpendicular to the axis of rotation to reconstruct an initial estimate of an object near the object's boundaries, synthesize a plurality of oblique projections by forward-projection, and combine the synthesized oblique projection samples and the measured oblique projection samples with the initial estimate of the object to produce a complete cone beam reconstruction.

In yet another aspect, a computer for collecting CT scan data is provided. The computer is programmed to position a gantry at a first position, collect a partial cone beam projection from a single source emitter at the first detector position such that the particular emitter defines a focal position in space, switch between a plurality of single source emitters as the gantry rotates so that the focal spot from which radiation emanates is substantially stationary in space, and collect a partial cone beam from a second emitter at a second detector position.

In another aspect, a computer for collecting CT scan data is provided. The computer is programmed to position a gantry at a first position, collect an inverted-cone beam projection at a first detector cell at the first gantry position such that the first detector cell defines a focusing position in space, move the gantry to a second position different from the first such that the source emitters are intermediate between the positions they occupied at the first gantry position, and collect an inverted-cone beam projection at the second gantry position, at a detector cell that occupies substantially the same point in space defined by the first detector cell during the first data collection cycle.

In still another aspect, a computed tomographic (CT) imaging system for collecting scan data is provided. The CT system includes a two-dimensional x-ray source emitter, a two-dimensional detector array, and a computer coupled to the two-dimensional detector array and the two-dimensional x-ray source emitter. The computer is programmed to position a gantry at a first position, collect a partial inverted-cone beam projection at a first detector cell at the first gantry position such that the first detector cell defines a focusing position in space, and collect data from a second detector cell different from the first detector cell as the gantry rotates such that the focusing position remains substantially stationary in space.

In yet another aspect, a computed tomographic (CT) imaging system for collecting scan data is provided. The CT system includes a two-dimensional x-ray source emitter, a two-dimensional detector array, and a computer coupled to the two-dimensional detector array and the two-dimensional x-ray source emitter. The computer is programmed to separate a sampling pattern into a plurality of simplified sampling geometries corresponding to inverted-cone beam trajectories of a plurality of individual detector elements, reconstruct an image volume for each inverted-cone beam trajectory, and combine the reconstructed image volumes into a final image based on a weighted summation of a plurality of the reconstructed image volumes.

In another aspect, a computed tomographic (CT) imaging system for collecting scan data is provided. The CT system includes a two-dimensional x-ray source emitter, a two-dimensional detector array, and a computer coupled to the two-dimensional detector array and the two-dimensional x-ray source emitter. The computer is programmed to collect x-ray projection samples that arise from x-rays that are perpendicular to the axis of rotation, collect x-ray projection samples that arise from x-rays that are oblique to the axis of rotation, utilize the projection samples arising from x-rays perpendicular to the axis of rotation to reconstruct an initial estimate of an object near the object's boundaries, synthesize a plurality of oblique projections by forward-projection, and combine the synthesized oblique projection samples and the measured oblique projection samples with the initial estimate of the object to produce a complete cone beam reconstruction.

In still another aspect, a computed tomographic (CT) imaging system for collecting scan data is provided. The CT system includes a two-dimensional x-ray source emitter, a two-dimensional detector array, and a computer coupled to the two-dimensional detector array and the two-dimensional x-ray source emitter. The computer is programmed to position a gantry at a first position, collect a partial cone beam projection from a single source emitter at the first detector position such that the particular emitter defines a focal position in space, switch between a plurality of single source emitters as the gantry rotates so that the focal spot from which radiation emanates is substantially stationary in space, and collect a partial cone beam from a second emitter at a second detector position.

In yet another aspect, a computed tomographic (CT) imaging system for collecting scan data is provided. The CT system includes a two-dimensional x-ray source emitter, a two-dimensional detector array, and a computer coupled to the two-dimensional detector array and the two-dimensional x-ray source emitter. The computer is programmed to position a gantry at a first position, collect an inverted-cone beam projection at a first detector cell at the first gantry position such that the first detector cell defines a focusing position in space, move the gantry to a second position different from the first such that the source emitters are intermediate between the positions they occupied at the first gantry position, and collect an inverted-cone beam projection at the second gantry position, at a detector cell that occupies substantially the same point in space defined by the first detector cell during the first data collection cycle.

DETAILED DESCRIPTION

In some known CT imaging system configurations, a radiation source projects a fan-shaped beam which is collimated to lie within an X-Y plane of a Cartesian coordinate system and generally referred to as an "imaging plane". The radiation beam passes through an object being imaged, such as a patient. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In third generation CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view". A "scan" of the object includes a set of views made at different gantry angles, or view angles, during one revolution of the radiation source and detector.

In an axial scan, the projection data is processed to construct an image that corresponds to a two dimensional slice taken through the object. One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a display device.

To reduce the total scan time, a helical scan may be performed. To perform a helical scan, the patient is moved while the data for the prescribed number of slices is acquired. Such a system generates a single helix from a fan beam helical scan. The helix mapped out by the fan beam yields projection data from which images in each prescribed slice may be reconstructed.

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
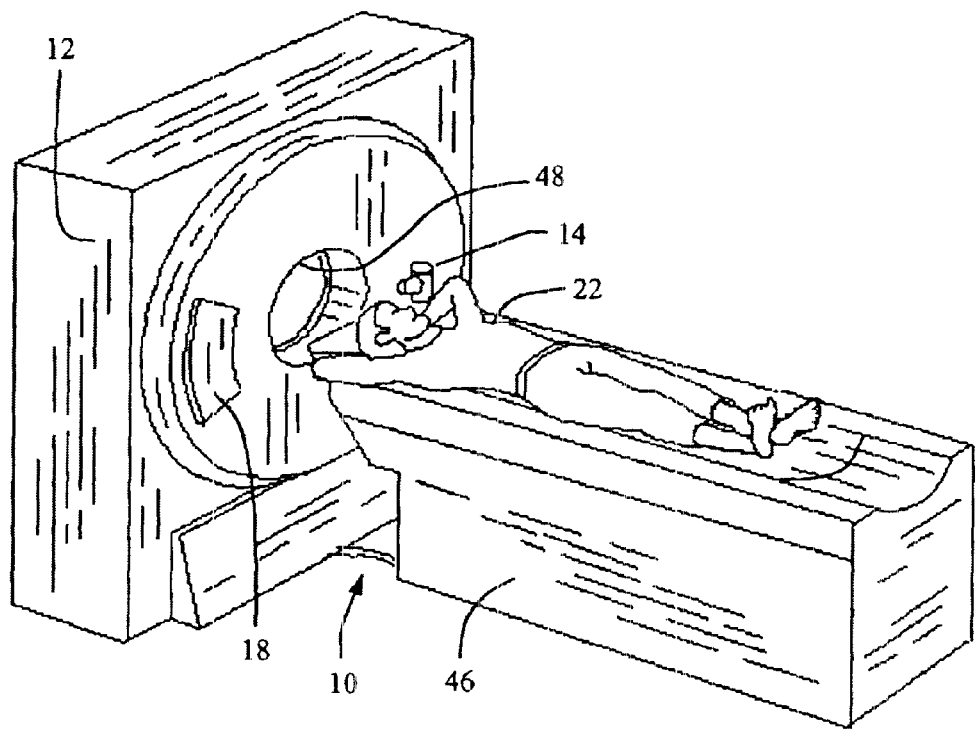
FIG. 1 is a pictorial view of a CT imaging system.
Figure 2:
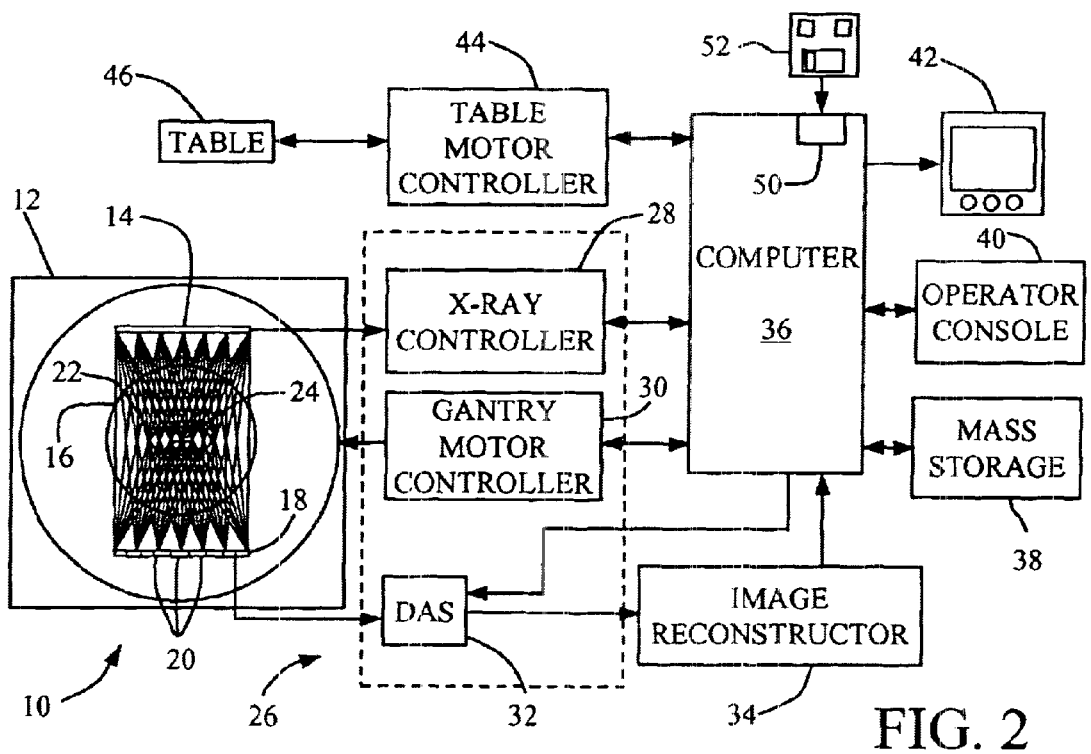
FIG. 2 is a block schematic diagram of the system illustrated in FIG. 1.

FIG. 1 is a pictorial view of a CT imaging system 10. FIG. 2 is a block schematic diagram of system 10 illustrated in FIG. 1. In the exemplary embodiment, a computed tomography (CT) imaging system 10, is shown as including a gantry 12 representative of a "third generation" CT imaging system. Gantry 12 has a radiation source 14 that projects a cone beam 16 of X-rays toward a detector array 18 on the opposite side of gantry 12. In one embodiment, radiation source 14 is a two-dimensional radiation source that projects a plurality of cone beams 16 from a plurality of locations on radiation source 14, also referred to herein as spots, toward detector 18 such that an inverted-cone beam geometry is received by detector 18.

Figure 3:
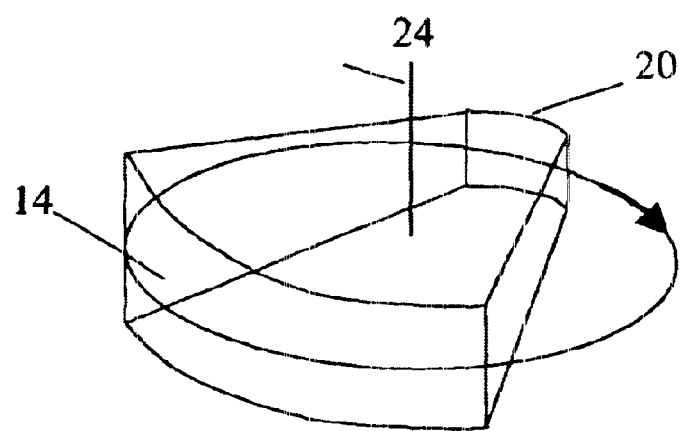
FIG. 3 is an illustration of the inverted cone geometry.

In another embodiment of the inverted cone geometry and as shown in FIG. 3, detector 20 is a two-dimensional array of detector elements or cells and is smaller than source 14. Source 14 is a planar, two-dimensional array of x-ray emitters which can be energized in any sequence or pattern. Each emitter serves as a single x-ray focal spot. Source 14 and detector 20 are stationary with respect to each other while the entire apparatus rotates about the center of rotation 24.

Detector array 18 is formed by a plurality of detector rows (not shown) including a plurality of detector elements 20 which together sense the projected X-ray beams that pass through an object, such as a medical patient 22. Each detector element 20 produces an electrical signal that represents the intensity of an impinging radiation beam and hence the attenuation of the beam as it passes through object or patient. 22. During a scan to acquire radiation projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 such that projection data corresponding to a plurality of quasi-parallel or parallel slices can be acquired simultaneously during a scan. Similarly, two-dimensional detector array 18 includes a two-dimensional detector elements array 20 such that projection data corresponding to a cone beam geometry can be acquired simultaneously.

Rotation of gantry 12 and the operation of radiation source 14 are governed by a control mechanism 26 of CT system 10. Control mechanism 26 includes a radiation controller 28 that provides power and timing signals to radiation source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized radiation data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36.

The operator supplied commands and parameters are used by computer 36 to provide control signals and information to DAS 32, radiation controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 4:
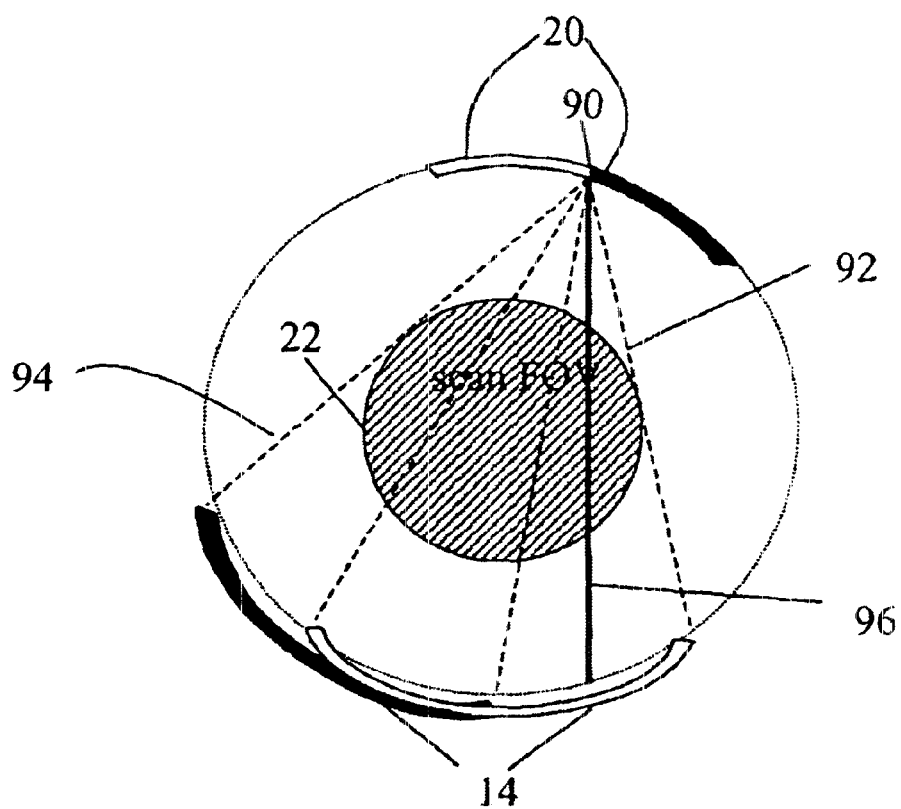
FIG. 4 is an illustration of one embodiment of the inverted cone scanning trajectory.

FIG. 4 is an illustration of an exemplary embodiment of a scanning trajectory that produces a single inverted-cone beam projection that is large enough to encompass the object or patient 22 in the scan field of view (FOV). As shown in FIG. 4, x-ray source 14 alone may not cover the desired scan FOV 22. An enlarged scan FOV is achieved by combining a plurality of overlapping inverted-cone beams which come to focus at the same point in space 90. At a first gantry 12 position a partial inverted-cone beam projection 92 is collected at a particular cell of detector 20, which defines a focusing position in space 90. As gantry 12 rotates, a partial inverted-cone beam projection 94 is collected from at least one different detector cell so that the focusing position 90 remains stationary in space. Such collection of partial inverted-cone beam projections can continue until the detector 20 is no longer aligned with the original focusing position in space 90. A plurality of partial inverted-cone beam projections are combined to form a single cone beam projection that covers the entire object or patient 22 in the scan FOV. While only a single inverted-cone beam has been depicted, in reality many inverted-cone beam projections are formed, with each detector cell corresponding to a new set of inverted-cone beam projections. FIG. 4 depicts two source-detector positions while all the intermediate positions are omitted for clarity.

In one embodiment, an individual ray-path 96 can be sampled at different time instants by a plurality of source 14 emitters and a plurality of detector 20 cells to collect data. For any of the inverted-cone beam sampling trajectories, the source emitters need to be switched on one at a time, since the detector cell is angular insensitive. That is, the detector cell is not capable of determining the incident angle of the x-ray photons because the photon signals are integrated over the sampling period. For the detectors that are capable of performing photon counting, there is a possibility that all emitters can be turned on at the same time and the detector will be used to identify the incident angle of each x-ray photon impinging on the detector cell. The collected data can be used to perform physiological gating, which in one embodiment includes selecting a plurality of samples collected in a same phase of a motion cycle to suppress motion-related image artifacts. The sampling of individual ray-paths allows for a reduced detector and x-ray source size, thereby reducing the cost and complexity of the system. The sampling of redundant ray-paths also allows for a relaxation of the specification requirements for the x-ray source and detector, automatic identification of at least one degraded detector cell by comparing the projection samples of the same ray-path, and better calibration of the system.

Figure 5:
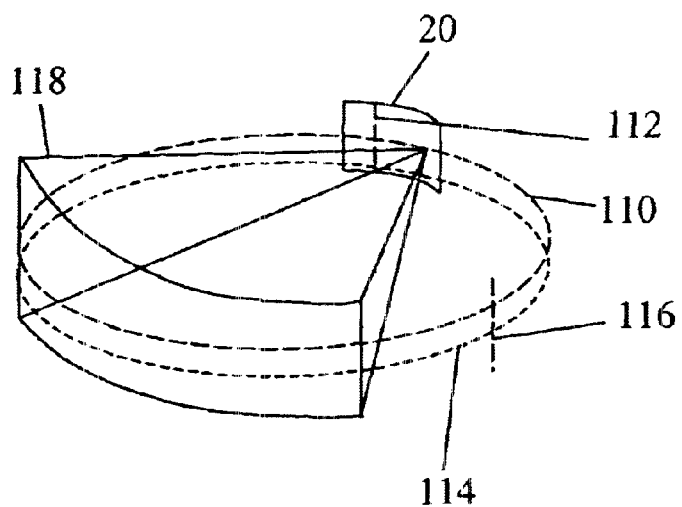
FIG. 5 is an illustration of the simplified scanning geometry of a circumferential line and a vertical line.
Figure 6:
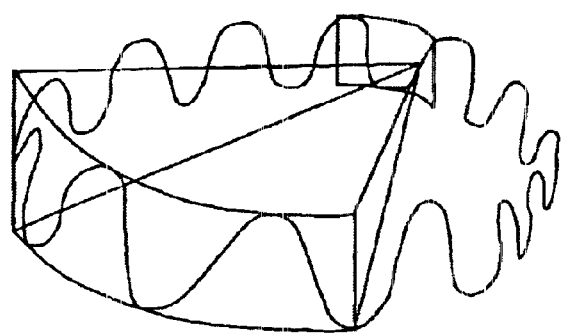
FIG. 6 is an illustration of the simplified scanning geometry of a sinusoidal circumferential line.

Referring to FIG. 5 and in another embodiment, the sampling patterns are broken into multiple, simple sampling geometries. For example, FIG. 5 illustrates a trajectory of a circumferential line 110 plus a vertical line 112, although other simple trajectories such as sinusoidal curves are also possible as shown in FIG. 6. Also depicted in FIG. 5 are the trajectory of a second circumferential line 114 and a corresponding vertical line 116. Samples collected by each detector 20 element form an inverted-cone beam projection 118 with a single circle trajectory. Detector 20 readings at the same gantry 12 location from other detector 20 elements that form a line 112 with the detector 20 element provide the required line segment. An image volume, $p_{ij}$ (x,y,z), can be reconstructed for each cone beam trajectory, where the subscripts i and j represent the detector element location and (x,y,z) are the image coordinates. Many studies have shown that projection datasets collected on circle-plus-line or sinusoidal trajectories produce much improved image quality as compared to the single circle trajectory. The final image, p (x,y,z), is then the weighted summation of all $p_{ij}$ (x,y,z):

$$p(x, y, z) = \sum_{i,j} w_{i,j} p_{i,j}(x, y, z)$$ [0042]

where $w_{i,j}$ is determined based on the quality of the reconstructed image set, which in turn can be based on the overall cone angle or the symmetry of the sampling of the object.

Figure 7:
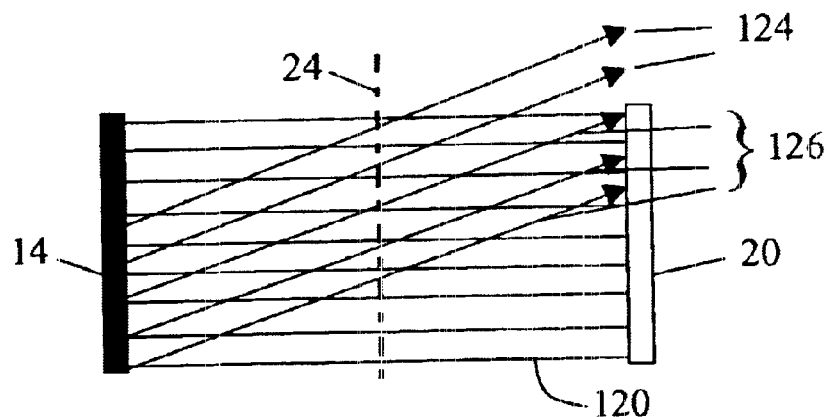
FIG. 7 is an illustration of ray paths that are perpendicular and oblique to the axis of rotation.

In another embodiment and as shown in FIG. 7, projection samples that arise from x-rays that are perpendicular 120 to the axis of rotation 24 are used to reconstruct an initial estimate of an object near its boundaries. Because a majority of the samples are oblique in nature, only a small fraction of the samples are used and the noise performance is not optimal. However, once an initial estimation of the object is obtained, any missing oblique projections 124 can be synthesized by forward-projection of the initial estimate. The synthesized projections 124 can then be combined with measured oblique samples 126 to produce a complete inverted-cone beam reconstruction.

Figure 8:
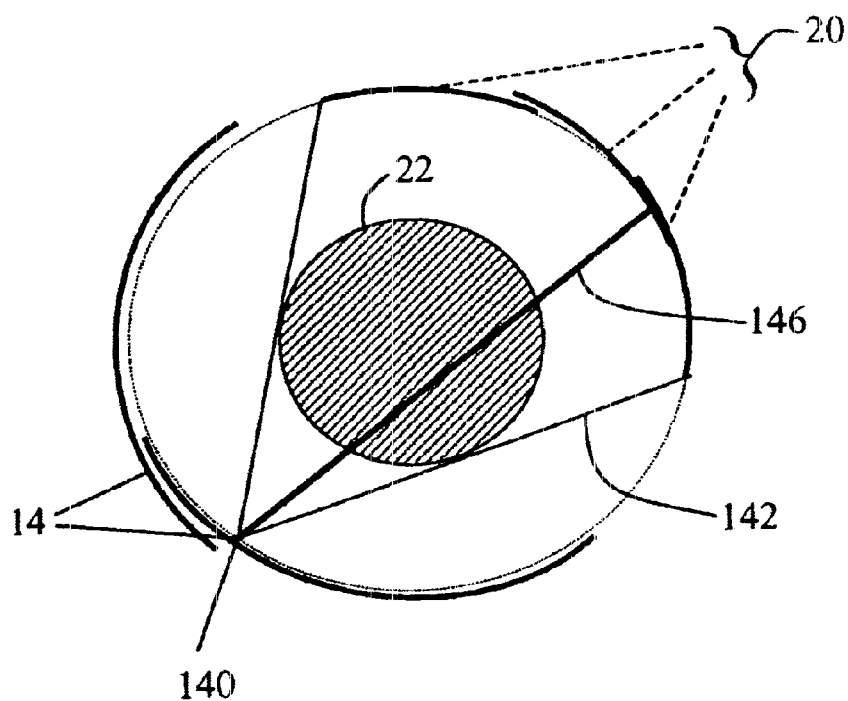
FIG. 8 is an illustration of one embodiment of detector-based cone beam sampling.

In another embodiment, which may be referred to as detector-based cone beam sampling, a single cone-beam projection is formed by combining projection measurements at different gantry positions. In this embodiment and as shown in FIG. 8, the x-ray emitters 14 are energized in a sequence so that a point of emission 140 remains substantially stationary in space as gantry 12 rotates. A single cone beam projection 142 is formed by combining projection measurements obtained at a plurality of gantry positions. As gantry 12 rotates, detector 20 array collects the x-ray attenuation data produced by cone beam 142. In one embodiment, detector 20 may be smaller than the cone-beam scan FOV 22 with the result that the x-ray attenuation data collected at each gantry position corresponds to a partial cone beam projection. In this case, a single cone-beam projection covering the entire scan FOV is formed by combining partial cone beam projection measurements obtained at a plurality of gantry positions. The combining of partial cone beam projections can be performed by blending a plurality of partial cone beam projections according to a weighting function, in order to suppress image artifacts. The redundant sampling obtained in this configuration can also be used to reduce the performance requirement on the detector and source, because the same ray-path is sampled multiple times by different detector and source spot, similar to the case described above.

While FIG. 8 shows only three distinct detector locations, in practice the detector rotates continuously around the trajectory. Therefore, many samples are collected and there are not boundaries between samples collected at different detector locations. As described above, a plurality of partial cone beam projections are combined to produce complete cone beam projections. In this manner, the entire projection is transitioned from one location to the next without significant differentiation in data collection conditions.

In one embodiment, an individual ray-path 146 can be sampled at different time instants by a plurality of source 14 emitters and a plurality of detector 20 cells to collect data. For this configuration emitters 14 are turned on one at a time. The collected data can be used to perform physiological gating, which in one embodiment includes selecting a plurality of samples collected in a same phase of a motion cycle to suppress motion-related image artifacts. Advantages of said sampling of individual ray-paths include permitting a reduced detector and x-ray source size, thereby reducing the cost and complexity of the system; a relaxation of the specification requirements for the x-ray source and detector; automatic identification of at least one degraded detector cell by comparing the projection samples of the same ray-path; and better calibration of the system.

Figure 9:
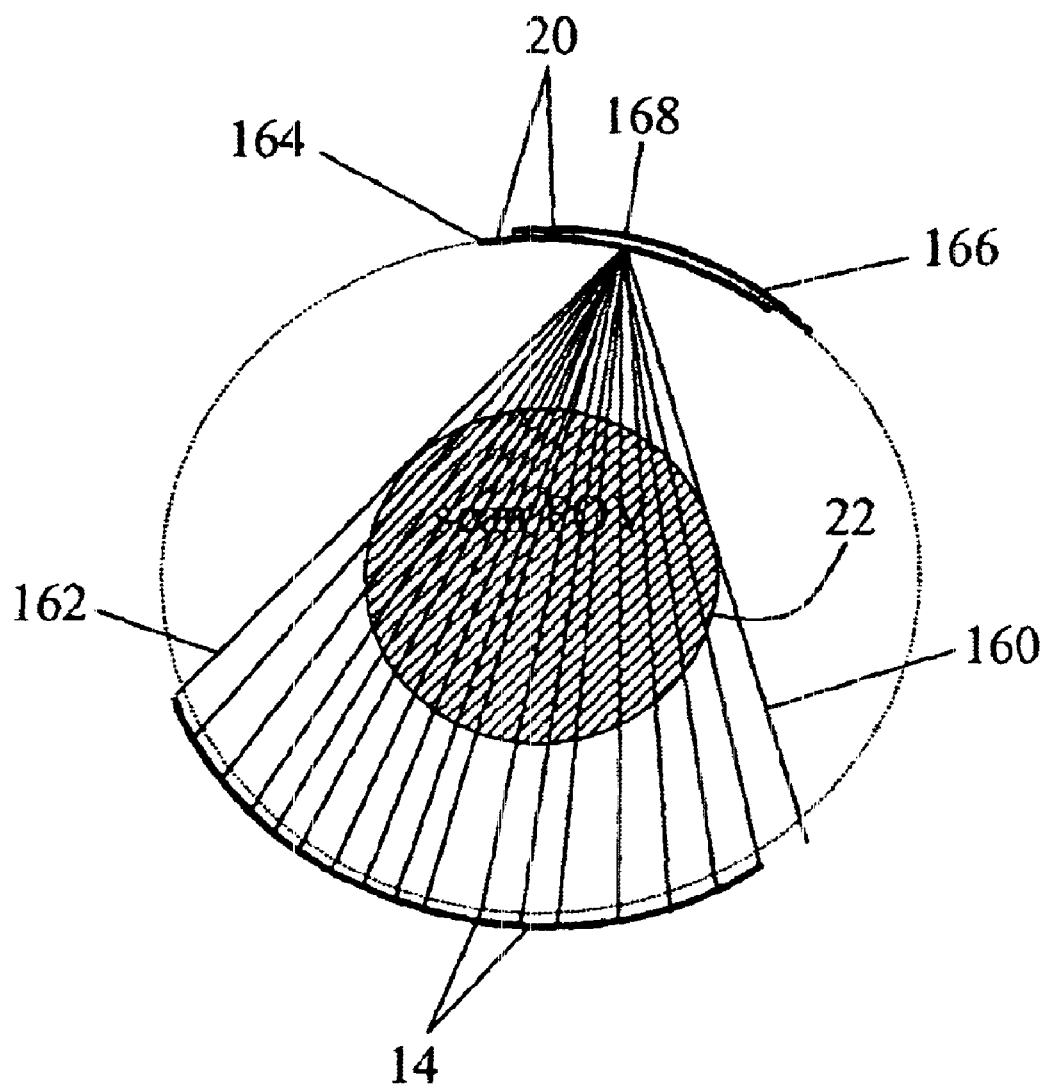
FIG. 9 is an illustration of collecting data with the source emitters at two non-overlapping positions.

Another embodiment, as shown in FIG. 9, provides for reducing aliasing artifacts due to the discrete nature of the two-dimensional x-ray source. Because the x-rays are emitted from discrete locations on the source array, the sampling pattern is similar to that of third generation CT scanners in which the sampling distance between adjacent rays is determined by the spacing between the detectors. In this embodiment and as shown in FIG. 9, data is collected from the sample at multiple source emitter 14 locations such that the positions of the x-ray sources at a particular emitter location are at intermediate locations relative to the positions of the x-ray sources at the previous emitter location, thereby reducing aliasing artifacts due to the presence of discrete x-ray sources. In this embodiment, the gantry 12 moves such that the detectors are in a first position 164, at which point an inverted-cone beam projection is collected at a first detector cell. The position of this first detector cell defines a focusing position in space 168. Gantry 112 is then moved to a second position different from the first such that a plurality source emitters 162 are intermediate between the positions they occupied at the first gantry position. An inverted-cone beam projection is then collected at the second gantry position at a detector cell that occupies substantially the same point in space 168 defined by the first detector cell during the first data collection cycle.

While FIG. 9 only depicts one set of inverted-cone beams, in use many sets of inverted-cone beams are formed corresponding to individual detector cells. In addition, while only one intermediate position of the x-ray emitters is shown, in use a plurality of intermediate positions of the x-ray emitters could be used to collect data to prevent aliasing artifacts.

While the invention has been described in terms of various specific embodiments, those skilled in the art will recognize that the invention can be practiced with modification within the spirit and scope of the claims.

What is claimed is:

1. A method for collecting computed tomography (CT) scan data, said method comprising:

positioning a gantry at a first position;

collecting a partial inverted-cone beam projection at a first detector cell at the first gantry position such that the first detector cell defines a focusing position in space; and collecting data from a second detector cell different from the first detector cell as the gantry rotates such that the focusing position remains substantially stationary in space.

2. A method in accordance with claim 1 further comprising combining a plurality of partial inverted-cone beam projections to form a single inverted-cone beam projection that covers the entire object in a scan field of view.

3. A method in accordance with claim 1 further comprising sampling a single ray-path at a plurality of time intervals by a plurality of source emitters and a plurality of detector cells to collect data.

4. A method in accordance with claim 3 further comprising using said data sampled at single ray-paths for physiological gating.

5. A method in accordance with claim 4 further comprising selecting a plurality of samples that are collected in a same phase of a motion cycle to suppress motion-related image artifacts.

6. A method in accordance with claim 3 further comprising using said data sampled at single ray-paths for identifying at least one degraded detector cell.

7. A method in accordance with claim 3 further comprising using said data sampled at single ray-paths for automatically identifying at least one degraded detector cell.

8. A method for collecting CT scan data, said method comprising:

separating a sampling pattern into a plurality of simplified sampling geometries corresponding to inverted-cone beam trajectories of a plurality of individual detector elements;

reconstructing an image volume for each inverted-cone beam trajectory; and combining the reconstructed image volumes into a final image based on a weighted summation of a plurality of said reconstructed image volumes.

9. A method in accordance with claim 8 wherein said combining of reconstructed image volumes further comprises combining a plurality of reconstructed image volumes, $p_{ij}$ (x,y,z), into a final image, p(x,y,z), based on a weighted summation of a plurality of $p_{ij}$ (x,y,z) in accordance with:

$$p(x, y, z) = \sum_{i,j} w_{i,j} p_{i,j}(x, y, z) \qquad [0042]$$

where:
i and j represent the detector element locations;
$w_{i,j}$ is a weighting factor for detector element (i,j); and
(x,y,z) are the coordinates of the reconstructed image volume.

10. A method in accordance with claim 9 wherein said weighting factor $w_{i,j}$ is based on an overall cone angle.

11. A method in accordance with claim 9 wherein said weighting factor $w_{i,j}$ is based on a symmetry of sampling.

12. A method in accordance with claim 8 wherein said simplified sampling geometry comprises a circumferential line and a vertical line.

13. A method in accordance with claim 8 wherein said simplified sampling geometry comprises a sinusoidal circumferential line.

14. A method for collecting CT scan data, said method comprising:

collecting x-ray projection samples that arise from x-rays that are perpendicular to the axis of rotation;

collecting x-ray projection samples that arise from x-rays that are oblique to the axis of rotation;

utilizing the projection samples arising from x-rays perpendicular to the axis of rotation to reconstruct an initial estimate of an object near the object's boundaries;

synthesizing a plurality of oblique projections by forward-projection; and combining the synthesized oblique projection samples and the measured oblique projection samples with the initial estimate of the object to produce a complete cone beam reconstruction.

15. A method for collecting CT scan data, said method comprising:

positioning a gantry at a first position;

collecting a partial cone beam projection from a single source emitter at the first detector position such that the particular emitter defines a focal position in space;

switching between a plurality of single source emitters as the gantry rotates so that the focal spot from which radiation emanates is substantially stationary in space; and collecting a partial cone beam from a second emitter at a second detector position.

16. A method in accordance with claim 15 further comprising combining a plurality of said partial cone beam projections to form a single cone beam projection.

17. A method in accordance with claim 16 wherein said combining partial cone beam projections is performed according to a weighting function.

18. A method in accordance with claim 15 further comprising sampling a single ray-path at a plurality of time intervals by a plurality of source emitters and a plurality of detector cells to collect data.

19. A method in accordance with claim 18 further comprising using said data sampled at single ray-paths for physiological gating.

20. A method in accordance with claim 19 further comprising selecting a plurality of samples that are collected in a same phase of a motion cycle to suppress motion-related image artifacts.

21. A method in accordance with claim 18 further comprising using said data sampled at single ray-paths for identifying at least one degraded detector cell.

22. A method in accordance with claim 18 further comprising using said data sampled at single ray-paths for automatically identifying at least one degraded detector cell.

23. A method for collecting CT scan data, said method comprising:

positioning a gantry at a first position;

collecting an inverted-cone beam projection at a first detector cell at the first gantry position such that the first detector cell defines a focusing position in space;

moving the gantry to a second position different from the first such that the source emitters are intermediate between the positions they occupied at the first gantry position; and collecting an inverted-cone beam projection at the second gantry position, at a detector cell that occupies substantially the same point in space defined by the first detector cell during the first data collection cycle.

24. A computer for collecting computed tomography (CT) scan data, said computer programmed to:
- position a gantry at a first position;
- collect a partial inverted-cone beam projection at a first detector cell at the first gantry position such that the first detector cell defines a focusing position in space; and
- collect data from a second detector cell different from the first detector cell as the gantry rotates such that the focusing position remains substantially stationary in space.

25. A computer in accordance with claim 24 further programmed to combine a plurality of partial inverted-cone beam projections to form a single inverted-cone beam projection that covers the entire object in a scan field of view.

26. A computer in accordance with claim 24 further programmed to sample a single ray-path at a plurality of time intervals by a plurality of source emitters and a plurality of detector cells to collect data.

27. A computer in accordance with claim 26 further programmed to use said data sampled at single ray-paths for physiological gating.

28. A computer in accordance with claim 27 further programmed to select a plurality of samples that are collected in a same phase of a motion cycle to suppress motion-related image artifacts.

29. A computer in accordance with claim 26 further programmed to use said data sampled at single ray-paths for identifying at least one degraded detector cell.

30. A computer in accordance with claim 26 further programmed to use said data sampled at single ray-paths for automatically identifying at least one degraded detector cell.

31. A computer for collecting CT scan data, said computer programmed to:
- separate a sampling pattern into a plurality of simplified sampling geometries corresponding to inverted-cone beam trajectories of a plurality of individual detector elements;
- reconstruct an image volume for each inverted-cone beam trajectory; and
- combine the reconstructed image volumes into a final image based on a weighted summation of a plurality of said reconstructed image volumes.

32. A computer in accordance with claim 31 wherein to combine reconstructed image volumes said computer further programmed to combine a plurality of reconstructed image volumes $p_{ij}(x,y,z)$, into a final image, $p(x,y,z)$, based on a weighted summation of a plurality of $p(x,y,z)$ in accordance with:

$$p(x, y, z) = \sum_{i,j} w_{i,j} p_{i,j}(x, y, z)$$

where:
- i and j represent the detector element locations;
- $w_{i,j}$ is a weighting factor for detector element (i,j); and
- (x,y,z) are the coordinates of the reconstructed image volume.

33. A computer in accordance with claim 32 wherein said computer is further programmed to weight factor $w_{i,j}$ based on an overall cone angle.

34. A computer in accordance with claim 32 wherein said computer is further programmed to weight factor $w_{i,j}$ based on a symmetry of sampling.

35. A computer in accordance with claim 31 wherein said computer is further programmed to simplify said sampling geometry to a circumferential line and a vertical line.

36. A computer in accordance with claim 31 wherein said computer is further programmed to simplify said sampling geometry comprises a sinusoidal circumferential line.

37. A computer for collecting CT scan data, said computer programmed to:
- collect x-ray projection samples that arise from x-rays that are perpendicular to the axis of rotation;
- collect x-ray projection samples that arise from x-rays that are oblique to the axis of rotation;
- utilize the projection samples arising from x-rays perpendicular to the axis of rotation to reconstruct an initial estimate of an object near the object's boundaries;
- synthesize a plurality of oblique projections by forward-projection; and
- combine the synthesized oblique projection samples and the measured oblique projection samples with the initial estimate of the object to produce a complete cone beam reconstruction.

38. A computer for collecting CT scan data, said computer programmed to:
- position a gantry at a first position;
- collect a partial cone beam projection from a single source emitter at the first detector position such that the particular emitter defines a focal position in space;
- switch between a plurality of single source emitters as the gantry rotates so that the focal spot from which radiation emanates is substantially stationary in space; and
- collect a partial cone beam from a second emitter at a second detector position.

39. A computer in accordance with claim 38 further programmed to combine a plurality of said partial cone beam projections to form a single cone beam projection.

40. A computer in accordance with claim 39 wherein said computer is programmed to combine partial cone beam projections according to a weighting function.

41. A computer in accordance with claim 38 further programmed to sample a single ray-path at a plurality of time intervals by a plurality of source emitters and a plurality of detector cells to collect data.

42. A computer in accordance with claim 41 further programmed to use said data sampled at single ray-paths for physiological gating.

43. A computer in accordance with claim 42 further programmed to select a plurality of samples that are collected in a same phase of a motion cycle to suppress motion-related image artifacts.

44. A computer in accordance with claim 41 further programmed to use said data sampled at single ray-paths for identifying at least one degraded detector cell.

45. A computer in accordance with claim 41 further programmed to use said data sampled at single ray-paths for automatically identifying at least one degraded detector cell.

46. A computer for collecting CT scan data, said computer programmed to:
- position a gantry at a first position;
- collect an inverted-cone beam projection at a first detector cell at the first gantry position such that the first detector cell defines a focusing position in space;
- move the gantry to a second position different from the first such that the source emitters are intermediate between the positions they occupied at the first gantry position; and collect an inverted-cone beam projection at the second gantry position, at a detector cell that occupies substantially the same point in space defined by the first detector cell during the first data collection cycle.

47. A computed tomographic (CT) imaging system for collecting scan data, said CT system comprising:
a two-dimensional x-ray source emitter;
a two-dimensional detector array; and
a computer coupled to said two-dimensional detector array and said two-dimensional x-ray source emitter, said computer programmed to:
position a gantry at a first position;
collect a partial inverted-cone beam projection at a first detector cell at the first gantry position such that the first detector cell defines a focusing position in space; and
collect data from a second detector cell different from the first detector cell as the gantry rotates such that the focusing position remains substantially stationary in space.

48. A computer in accordance with claim 47 further programmed to combine a plurality of partial inverted-cone beam projections to form a single inverted-cone beam projection that covers the entire object in a scan field of view.

49. A computer in accordance with claim 47 further programmed to sample a single ray-path at a plurality of time intervals by a plurality of source emitters and a plurality of detector cells to collect data.

50. A computer in accordance with claim 49 further programmed to use said data sampled at single ray-paths for physiological gating.

51. A computer in accordance with claim 50 further programmed to select a plurality of samples that are collected in a same phase of a motion cycle to suppress motion-related image artifacts.

52. A computer in accordance with claim 49 further programmed to use said data sampled at single ray-paths for identifying at least one degraded detector cell.

53. A computer in accordance with claim 49 further programmed to use said data sampled at single ray-paths for automatically identifying at least one degraded detector cell.

54. A computed tomographic (CT) imaging system for collecting scan data, said CT system comprising:
a two-dimensional x-ray source emitter;
a two-dimensional detector array; and
a computer coupled to said two-dimensional detector array and said two-dimensional x-ray source emitter, said computer programmed to:
separate a sampling pattern into a plurality of simplified sampling geometries corresponding to inverted-cone beam trajectories of a plurality of individual detector elements;
reconstruct an image volume for each inverted-cone beam trajectory; and combine the reconstructed image volumes into a final image based on a weighted summation of a plurality of said reconstructed image volumes.

55. A computer in accordance with claim 54 wherein to combine reconstructed image volumes said computer further programmed to combine a plurality of reconstructed image volumes $p_{ij}(x,y,z)$, into a final image, $p(x,y,z)$, based on a weighted summation of a plurality of p (x,y,z) in accordance with:

$$p(x, y, z) = \sum_{i,j} w_{i,j} p_{i,j}(x, y, z)$$

where:
i and j represent the detector element locations;
$w_{i,j}$ is a weighting factor for detector element (i,j); and
(x,y,z) are the coordinates of the reconstructed image volume.

56. A computer in accordance with claim 55 wherein said computer is further programmed to weight factor $w_{i,j}$ based on an overall cone angle.

57. A computer in accordance with claim 55 wherein said computer is further programmed to weight factor $w_{i,j}$ based on a symmetry of sampling.

58. A computer in accordance with claim 54 wherein said computer is further programmed to simplify said sampling geometry to a circumferential line and a vertical line.

59. A computer in accordance with claim 54 wherein said computer is further programmed to simplify said sampling geometry comprises a sinusoidal circumferential line.

60. A computed tomographic (CT) imaging system for collecting scan data, said CT system comprising:
a two-dimensional x-ray source emitter;
a two-dimensional detector array; and
a computer coupled to said two-dimensional detector array and said two-dimensional x-ray source emitter, said computer programmed to:
collect x-ray projection samples that arise from x-rays that are perpendicular to the axis of rotation;
collect x-ray projection samples that arise from x-rays that are oblique to the axis of rotation;
utilize the projection samples arising from x-rays perpendicular to the axis of rotation to reconstruct an initial estimate of an object near the object's boundaries;
synthesize a plurality of oblique projections by forward-projection; and
combine the synthesized oblique projection samples and the measured oblique projection samples with the initial estimate of the object to produce a complete cone beam reconstruction.

61. A computed tomographic (CT) imaging system for collecting scan data, said CT system comprising:
a two-dimensional x-ray source emitter;
a two-dimensional detector array; and
a computer coupled to said two-dimensional detector array and said two-dimensional x-ray source emitter, said computer programmed to:
position a gantry at a first position;
collect a partial cone beam projection from a single source emitter at the first detector position such that the particular emitter defines a focal position in space;
switch between a plurality of single source emitters as the gantry rotates so that the focal spot from which radiation emanates is substantially stationary in space; and
collect a partial cone beam from a second emitter at a second detector position.

62. A computer in accordance with claim 61 further programmed to combine a plurality of said partial cone beam projections to form a single cone beam projection.

63. A computer in accordance with claim 62 wherein said computer is programmed to combine partial cone beam projections according to a weighting function.

64. A computer in accordance with claim 61 further programmed to sample a single ray-path at a plurality of time intervals by a plurality of source emitters and a plurality of detector cells to collect data.

65. A computer in accordance with claim 64 further programmed to use said data sampled at single ray-paths for physiological gating.

66. A computer in accordance with claim 65 further programmed to select a plurality of samples that are collected in a same phase of a motion cycle to suppress motion-related image artifacts.

67. A computer in accordance with claim 64 further programmed to use said data sampled at single ray-paths for identifying at least one degraded detector cell.

68. A computer in accordance with claim 64 further programmed to use said data sampled at single ray-paths for automatically identifying at least one degraded detector cell.

69. A computed tomographic (CT) imaging system for collecting scan data, said CT system comprising:

a two-dimensional x-ray source emitter;

a two-dimensional detector array; and a computer coupled to said two-dimensional detector array and said two-dimensional x-ray source emitter, said computer programmed to:

position a gantry at a first position;

collect an inverted-cone beam projection at a first detector cell at the first gantry position such that the first detector cell defines a focusing position in space;

move the gantry to a second position different from the first such that the source emitters are intermediate between the positions they occupied at the first gantry position; and collect an inverted-cone beam projection at the second gantry position, at a detector cell that occupies substantially the same point in space defined by the first detector cell during the first data collection cycle.

* * * * *